US006803035B2

(12) United States Patent
Greenblatt et al.

(10) Patent No.: US 6,803,035 B2
(45) Date of Patent: Oct. 12, 2004

(54) ANTI-DIARRHEAL AND METHOD FOR USING THE SAME

(75) Inventors: Hellen Chaya Greenblatt, Wilmington, DE (US); Orn Adalsteinsson, Kennett Square, PA (US); David A. Brodie, East Windsor, NJ (US); Henry Jacoby, Brigantine, NJ (US)

(73) Assignee: Arkion Life Sciences, Wilmington, DE (US)

( * ) Notice: Subject to any disclaimer, the term of this patent is extended or adjusted under 35 U.S.C. 154(b) by 0 days.

(21) Appl. No.: 10/054,067

(22) Filed: Jan. 22, 2002

(65) Prior Publication Data

US 2003/0068314 A1 Apr. 10, 2003

Related U.S. Application Data

(63) Continuation-in-part of application No. 09/291,784, filed on Apr. 14, 1999, now abandoned.
(60) Provisional application No. 60/084,765, filed on May 8, 1998, now abandoned.

(51) Int. Cl.[7] ........................ A61K 31/74; A61K 39/40; A61K 39/42; A61K 39/395; A61K 39/38
(52) U.S. Cl. ................. 424/78.01; 424/78.01; 424/130.1; 424/134.1; 424/147.1; 424/150.1; 424/151.1; 424/156.1; 424/163.1; 424/164.1; 424/165.1; 424/170.1; 424/178.1; 424/184.1; 424/201.1; 424/278.1; 424/520; 424/581; 435/69.3; 435/71.1; 435/130.1; 435/164.1; 435/165.1; 435/184.1; 435/201.1; 435/202.1; 435/203.1; 435/239; 435/278.1; 435/325; 435/326; 435/339; 435/340; 435/342; 435/345

(58) Field of Search ................. 435/69.3, 71.1, 435/71.3, 183, 239, 325, 326, 339, 339.1, 340, 342, 345; 424/130.1, 134.1, 147.1, 150.1, 151.1, 156.1, 163.1, 164.1, 165.1–170.1, 178.1, 184.1, 201.1, 202.1, 278.1, 520, 581

(56) References Cited

U.S. PATENT DOCUMENTS

| 4,357,272 A | * | 11/1982 | Polson | 260/112 |
| 5,080,895 A | * | 1/1992 | Tokoro et al. | 424/85.8 |
| 5,215,746 A | * | 6/1993 | Stolle et al. | 424/92 |
| 5,420,253 A | * | 5/1995 | Emery et al. | 530/423 |
| 5,593,972 A | * | 1/1997 | Weiner et al. | 514/44 |
| 5,601,823 A | * | 2/1997 | Williams | 424/167 |
| 5,753,228 A | * | 5/1998 | Sterling et al. | 424/151.1 |

* cited by examiner

*Primary Examiner*—Lynette R. F. Smith
*Assistant Examiner*—J. Hines
(74) *Attorney, Agent, or Firm*—RatnerPrestia

(57) ABSTRACT

A food product and method for treating and preventing diarrhea in a subject animal suffering from or susceptible to diarrhea. The method comprises administering an egg product to the subject animal wherein the egg product is obtained from a hyperimmunized avian.

11 Claims, No Drawings

ANTI-DIARRHEAL AND METHOD FOR USING THE SAME

RELATED APPLICATION

This application is a Continuation-in-Part of Provisional Application Ser. No. 60/084,765, filed May 8, 1998, now abandoned and U.S. application Ser. No. 09/291,784, filed Apr. 14, 1999, now abandoned.

FIELD OF THE INVENTION

This invention relates to a product and method for treating and preventing diarrhea and diarrheal symptoms. More particularly, this invention relates to a natural food product which, when administered to a subject animal, treats and prevents diarrhea and diarrheal symptoms in that subject animal.

BACKGROUND OF THE INVENTION

Diarrhea is a worldwide problem for individuals of all ages. Diarrhea is a common condition, which at the very least is life disrupting and can be life threatening. Acute diarrhea can be produced by a variety of pathological organisms, functional disruptions of intestinal function and as a drug-related side effect.

Some of the conditions in which diarrhea occurs are infant diarrhea (e.g., rotavirus-induced), childhood diarrhea, organism induced diarrhea (i.e. food poisoning), most gastrointestinal disorders, and diseases which affect the gastrointestinal system indirectly. Infants and children suffering from diarrhea have a major problem since they can become severely dehydrated and require fluids and medication.

Diarrhea is also common in cancer patients and may interfere with cancer treatment (Ippoliti, 1998). Chemotherapy, radiation therapy, surgery, graft-versus-hot disease (GVHD), bone marrow transplantation, or infection may induce diarrhea. Bacterial pathogens may also produce diarrheal symptoms with a spectrum of effects ranging from severe tissue damage to a lack of perceptible damage. Enterotoxigenic *Escherichia coli* which causes acute and severe diarrhea, does so by producing potent toxins, which act by altering the biological activity in epithelial cells. (Isaacson, 1998).

Current treatment of diarrhea consists of antibiotic treatment of the causative organisms or pharmacological intervention in pathophysiological function. Antidiarrheal drugs reduce the symptoms of diarrhea (loose stool consistency, frequency of defecation and excessive stool weight) by effects on intestinal transit, mucosal transport or luminal contents (Schiller, 1995). Opioids such as loperamide are the most useful antidiarrheal agents and act by a combination of inhibition of intestinal transit, pro-absorptive and anti-secretory effects. Other useful pharmacological therapies include use of alpha-adrenergic agonists such as clonidine and somatostatin analogues. These drugs may modify mucosal transport in addition to slowing transit but have limited clinical utility due to nonspecificity of action. Adsorbents (KAOPECTATE®), bismuth (PEPTO-BISMOL®) and stool texture modifiers are used frequently as over the counter medication, but their efficacy, other than PEPTO-BISMOL®, is largely unproven.

A safe and effective natural anti-diarrheal agent would be very useful in therapy of acute and chronic diarrheal conditions.

SUMMARY OF THE INVENTION

The invention is based upon the inventors' discovery that there is anti-diarrheal activity in egg or egg products and particularly in egg products obtained from hyperimmunized avians, which when administered to a subject animal, prevents or reduces diarrhea in that subject animal.

In particular, the invention is directed to a method of treating and preventing diarrheal symptoms in a subject animal, the method comprising administering to the subject animal an effective amount of egg product wherein said egg product comprises one or more anti-diarrheal agents, wherein said one or more anti-diarrheal agents comprises a substance other than an antibody.

DESCRIPTION OF THE INVENTION

The hyperimmune egg product of the invention, when administered to a subject animal, is useful for the treatment and prevention of diarrhea and diarrheal symptoms in that subject animal.

Terminology:

The term "diarrhea" or "diarrheal symptoms" means abnormal frequency and liquidity of fecal discharges resulting from an imbalance between absorption and secretion in the intestine.

The term "hyperimmunization" means exposure to one or more immunogenics such that an immune response is elevated and maintained above the natural unexposed state.

The terms "egg" or "egg product" each mean any whole egg (table, hyperimmunized or otherwise) or any product or fraction derived therefrom.

The terms "table egg" or "table egg product" each mean a whole egg, or any product or fraction derived therefrom, obtained from egg-producing animals which are not maintained in a hyperimmune state.

The terms "hyperimmune egg" or hyperimmune egg product" each mean whole egg or any product or fraction derived therefrom, obtained from an egg producing animal maintained in a hyperimmune state.

The term "supranormal levels" means levels in excess of those found in eggs of egg-producing animals not maintained in a hyperimmune state.

The term "immunogen" means a substance that is able to induce a humoral antibody and/or cell-mediated immune response rather than immunological tolerance. The term signifies the ability to stimulate an immune response as well as react with the products of it, e.g., antibody.

The term "combinatorial derived immunogens" refers to a novel process of generating molecular diversity among immunogenics by way of combinatorial synthesis.

The term "bioengineered immunogens" refers to immunogens which are obtained through the process of gene cloning technologies and genetic rearrangements which allow the insertion of encoding nucleotides which can give rise to molecules having immunogenicic properties.

The term "genetic vaccine" refers to a nucleic acid vaccine which is generally produced by recombinant technologies and which may elicit an immune response.

The term "treatment" means that the onset of the symptoms (including pain) of the disorder and/or pathogenic origin of the disorder be delayed or completely prevented, or, if present, the symptoms be ameliorated or completely eliminated. For example, the hyperimmune egg product treats arthritis and/or an autoimmune disease not only by suppressing the symptoms of the disorder in humans and other mammals, but also by acting as a prophylactic agent to counteract the presence of the disorder in the recipient.

The term "prevention" means that the progression of the disease is reduced and/or eliminated, or that the onset of the disease is eliminated.

The term "administer" means any method of providing a subject with a substance, including orally, intranasally, parenterally (intravenously, intramuscularly, or subcutaneously), rectally or topically.

The term "animal" means the animal kingdom definition.

The term "target animal" refers to an animal which functions as the egg or egg product producing animal.

The term "subject animal" refers to the animal which is administered the egg or egg product produced by the target animal.

The term "anti-diarrheal agent(s)" refers to certain agents or immune factors present in the hyperimmune egg or hyperimmune egg product of the invention that have an effect on the cells of the gastrointestinal tract, resulting in the inhibition of diarrhea and diarrheal symptoms. The anti-diarrheal agents are not antibodies.

The Invention

The hyperimmune egg product of the invention, when administered to a subject animal, is useful in treating and preventing diarrhea and diarrheal symptoms in the subject animal.

The product and method of the invention relate particularly to the use of hyperimmune egg product, which is a natural food product, in the treatment and prevention of diarrhea and diarrheal symptoms in a subject animal. Being natural, this food product can be used to treat and prevent diarrhea and diarrheal symptoms without the fear of side effects. Those allergic to eggs or having an intolerance to eggs may not be able to ingest the hyperimmune egg product in certain administerable forms.

In a preferred embodiment, the invention comprises a hyperimmune egg or egg product, and any fraction thereof, which is obtained from an egg-producing animal, and more preferably, an avian, which has been hyperimmunized with at least one immunogen. The hyperimmune egg product is one which is preferably administered orally to the subject animal although the hyperimmune egg or egg product can be further separated into more potent fractions which can subsequently be administered to a subject animal in a variety of forms.

The hyperimmune egg, egg product or fraction thereof of the invention, when administered to a subject animal, is effective in treating and preventing diarrheal symptoms, in that subject animal, resulting from, but not limited to, any of the following: acute and chronic diarrheal diseases such as infant diarrhea (e.g. including those diarrheas that are viral or bacteria induced), childhood diarrhea, adult organism induced diarrhea, and gastrointestinal disorder induced diarrhea, among others.

Hyperimmune Egg Product

The hyperimmune egg product can be produced by any egg-producing animal. It is preferred that the animal be a member of the class Aves or, in other words, an avian. Within the class Aves, domesticated fowl are preferred, but other members of this class, such as turkeys, ducks, and geese, are a suitable source of hyperimmune egg product.

When such egg-producing animals are brought to a specific state of immunization by means of, for example, hyperimmunization through periodic booster administrations of immunogenics, the animals will produce eggs having beneficial properties that, when consumed by a subject, such beneficial properties will treat and prevent diarrhea and diarrheal symptoms in that subject.

It is the inventors' belief that the beneficial properties referred to above are due to certain anti-diarrheal agents that are elicited via the hyperimmunization process. These anti-diarrheal agents are not believed to be antibodies, as the egg product of the invention was effective in inhibiting castor-oil induced diarrhea (see Example 2). The anti-diarrheal agents are therefore believed to be immune modulating factors that effectively induce the cellular arm of the immune response, resulting in the inhibition of diarrheal symptoms, regardless of the cause. Alternatively stated, the anti-diarrheal agents address the symptom of diarrhea, not the cause of the diarrhea.

This special state of hyperimmunization is preferably achieved by administering an initial immunization, followed by periodic boosters with sufficiently high doses of specific immunogens or mixtures of immunogens. The preferred dosage of booster should be equal to or greater than 50% of the dosage necessary to produce primary immunization of the avian. Thus, there is a threshold booster dosage below which the properties are not produced in the avian's egg, even though the avian is in what normally would be called an immune state.

Having knowledge of the requirement for developing and maintaining a hyperimmune state, it is within the skill of the art to vary the amount of immunogen administered, depending on the egg-producing animal genera and strain employed, in order to maintain the animal in the hyperimmune state.

The hyperimmune state is preferably produced by any immunogen or combination of immunogens. Hyperimmunization is preferably achieved by multiple exposures to multiple immunogens, multiple exposure to single immunogens, or single exposures to libraries of immunogens.

In addition to immunizations with naturally occurring immunogens, immunization may also be accomplished using immunogens which are synthetically derived by combinatorial chemistries. The basic strategy is to assemble multiple combinations of chemical building blocks for producing a population of molecules with diversity. Several methods have recently been developed for solid and solution phase combinatorial synthesis of libraries of oligomers (Fodor, S. et al., Science 251:767 (1991); Houghton, R. et al., Nature 354:82 (1991) as well as small organic molecules (Bunin, B. & Ellman, J., J. Am. Chem. Soc. 114:10997 (1992)). Rapid multiple peptide and oligomer synthesis can serve as a source for combinatorial derived immunogens. Furthermore, an alternative strategy would allow the addition of organic building blocks in combinatorial fashion to a backbone molecule for improved immunogenicity.

Alternative modes of hyperimmunizing egg producing animals can be used in place of immunogenic vaccines and include the use of genetic vaccines. In particular, any DNA construct (generally consisting of a promoter region and an immunogen encoding sequence) will trigger an immune response. Genetic vaccines consist of immunogenic-coding vectors, fragments of naked DNA, plasmid DNA, DNA-RNA immunogens, DNA-protein conjugates, DNA-liposome conjugates, DNA expression libraries, and viral and bacterial DNA delivered to produce an immune response. Methods of DNA delivery include particle bombardment, direct injection, viral vectors, liposomes and jet injection, among others. When applying these delivery methods, much smaller quantities may be necessary and generally result in more persistent immunogen production. When using such genetic processes, the preferred method for introducing DNA into avians is through intramuscular injection of the DNA into the breast muscle.

Methods of DNA delivery include but are not limited to, particle bombardment, direct injection, liposomes, jet injection (Fynan, E. F. et al., Proc. Natl. Acad. Sci. USA 90:11478–11482 (1993)). The nucleic acids that code for known or unknown immunogens, promoter regions (notably CMV cauliflower mosaic virus) and SV40 bacterial origin can be replicated in bacteria to produce plasmid DNA for use in DNA injections. Although several routes of parenteral administration of the DNA are effective in chickens, the preferred method is intramuscular injection to the breast muscle. Vaccine trials are carried out in egg laying avians, preferably chickens. Repeated immunizations are given at one to two week intervals for up to six months.

It is preferred that the amounts of DNA used are generally in the order of 50–300 μg of DNA in saline for direct injection. For particle bombardment, 4–100 μg of DNA co-precipitated onto gold beads by the addition of 2.5 M $CaCl_2$ are preferred. Repeated immunizations can be given intradermally by this method of accelerating DNA coated particles into the live animal.

Hyperimmunization Procedure

The following list of steps is an example of a preferred procedure used to bring an egg-producing animal to a heightened state of immunity from which the resultant hyperimmune egg or egg product can be administered to a subject:

1. Selecting one or more immunogens.
2. Eliciting an immune response in the egg-producing animal by primary immunization.
3. Administering booster vaccines of immunogens of appropriate dosage to induce and maintain the hyperimmune state.

Step 1: Any immunogen or combination of immunogens may be employed as a vaccine. The immunogens can be bacterial, viral, protozoan, fungal, cellular, or any other substances to which the immune system of an egg-producing animal will respond. The critical point in this step is that the immunogen(s) must be capable of inducing immune and hyperimmune states in the egg-producing animal. Although only a single immunogen may function as the vaccine for the method of the invention, one preferred vaccine is a mixture of polyvalent bacterial and fungal immunogens selected from the following immunogenic families: the enteric bacilli and bacteroides, pneumococci, Pseudomonas, Salmonella, Streptococci, bacilli, Staphylococci, Neisseria, Clostridia, Mycobacteria, Actinomycetes Chlamydiae, and Mycoplasma. Viral immunogens are preferably selected from the following immunogenic families: adenoviruses, picornaviruses and herpes viruses, although other viral immunogenic families will work.

In an alternative embodiment, a polyvalent vaccine referred to as Series 100 (S-100) is used. The bacteria included in the S-100 vaccine are listed in table 1 of Example 1. This vaccine has been previously described in U.S. Pat. Nos. 5,106,618 and 5,215,746, both assigned to Stolle Research and Development Corporation.

Step 2: The vaccine can be either a killed or live-attenuated vaccine and can be administered by any method that elicits an immune response. It is preferred that immunization be accomplished by administering the immunogens through intramuscular injection. The preferred muscle for injection in an avian is the breast muscle. Dosage is preferably 0.05–5 milligrams of the immunogenic vaccine. Other methods of administration that can be used include intravenous injection, intraperitoneal injection, intradermal, rectal suppository, aerosol or oral administration. When DNA techniques are used for the hyperimmunization process, much smaller quantities are required, generally 300 micrograms.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating immunogens, and tests designed to evaluate the ability of immune cells from the host to respond to the immunogen. The minimum dosage of immunogen necessary to induce an immune response depends on the vaccination procedure used, including the type of adjuvants and formulation of immunogen(s) used as well as the type of egg-producing animal used as the host.

Step 3: The hyperimmune state is preferably induced and maintained in the target animal by repeated booster administrations of an appropriate dosage at fixed time intervals. The time intervals are preferably 2–8 week intervals over a period of 6–12 months. However, it is essential that the booster administrations do not lead to immune tolerance. Such processes are well known in the art.

It is possible to use other hyperimmunization maintenance procedures or combination of procedures, such as, for example, intramuscular injection for primary immunization and intravenous injection for booster injections. Further procedures include simultaneously administering microencapsulated and liquid immunogen, or intramuscular injection for primary immunization, and booster dosages by oral administration or parenteral administration by microencapsulation means. Several combinations of primary and hyperimmunization are known to those skilled in the art.

Processing and Administration

Once the egg-producing animals have been sufficiently hyperimmunized, it is preferred that the eggs from these animals are collected and processed to produce a hyperimmune egg product in administerable form. Subsequently, the hyperimmune egg product can be administered to the subject.

The egg and/or egg product of the present invention is administered to a subject animal by any means that treats or prevents diarrhea or diarrheal symptoms in the subject animal. It is preferred that administration occurs by directly feeding the egg or any derivative of the egg. Egg and egg yolk are natural food ingredients and are non-toxic and safe.

In one embodiment, the egg product of the invention is integrated into a dietary supplement. One preferred method for preparing the egg of the invention to be incorporated into a dietary supplement involves drying the egg into an egg powder. Although various methods are known for drying eggs, spray drying is a preferred method. The process of spray drying eggs is well known in the art.

The dried egg powder can be incorporated into a variety of administerable forms, such as drinks in the form of, for example, protein powders, power building drinks, protein supplements and any other nutritional, athlete-associated products. In addition, the egg powder can be used in bake mixes, power bars, candies, cookies, etc. Alternatively, the egg powder can be placed in a capsule form and administered as such. Other examples of egg processing include making an omelet, soft or hard-boiling the egg, baking the egg, or, if desired, the egg can be eaten raw or processed as liquid egg.

Finally, it is generally known that the yolk and/or white fractions contain the agent or agents responsible for the beneficial properties observed and referred to above. Those having ordinary skill in the art would clearly recognize that further separation could provide more potent fractions or elimination of undesirable components, and would allow for other modes of administration such as administering egg product parenterally, subcutaneously, intravenously, intramuscularly, intraperitoneally, intranasally, orally or topically. Such further separation will provide for the ability to make encapsulated products and pharmaceutical compositions with said egg or fraction thereof.

In order to determine the efficiency of the hyperimmunized egg product in treating and preventing diarrhea, the inventors used an animal model of diarrhea. The resulting data suggest that a high dose of hyperimmune egg product can both prevent and treat diarrhea in a well-known animal model referred to as castor oil administration, and described below (See Example 2).

Inhibition of castor oil induced diarrhea has been used as an animal model for the development of antidiarrheal agents such as diphenoxylate and loperamide and has been shown to be a good predictor of anti-diarrheal activity in humans for at least 25 years (Awouters et al, 1974). The present study indicates that acute dosing with egg obtained from chickens immunized against a variety of immunogens can inhibit castor oil induced diarrhea.

The mechanism of the diarrheogenic activity of castor oil is complex. Castor oil must first be metabolized to ricinoleic acid in the lumen of the intestinal tract. Ricinoleic acid then produces a marked increase in net secretion of fluid and electrolytes in the intestine resulting in diarrhea. The mechanism of action of castor oil has been studied recently by Mascolo N et al who found an activation of Platelet Activating Factor (PAF) in duodenal tissue by nitric oxide (NO) released in response to castor oil.

The study detailed in Example 2 shows that long periods of pretreatment are not needed for showing activity of the hyperimmune egg product and that the hyperimmune egg product is effective when given orally in a bolus dose. Thus it is the inventors' conclusion that hyperimmune egg product is a safe and effective therapy for alleviation of acute or chronic diarrhea irrespective of cause and may be a valuable addition to therapy in diarrheal conditions. The study showed that when hyperimmune egg product is given by oral bolus doses for two days, it will significantly inhibit castor oil-induced diarrhea in a mouse.

When it comes to treatment and prevention of the diarrheal disorder, the hyperimmune egg product is preferably administered to the subject in an amount that is immunologically effective in treating and preventing the particular disorder. A dose-related effect was seen when doses of 1,2 and 4 grams/kg were administered in the castor oil study. Dosage and duration of the administration, however, will depend upon the particular condition, whether it is present, and, if so, the advancement of the condition in the subject. It is preferred that the hyperimmune egg product is provided in whatever amount is necessary and effective in treating and/or preventing the condition and the symptoms of the condition. For example, in some cases, daily amounts ranging from less than one to several whole, hyperimmune eggs (or hyperimmune egg products containing the equivalent of less than one to several whole, hyperimmune eggs) can be administered to the subject depending on the particular circumstance of the condition. More potent fractions can be separated and concentrated by methods well-known in the art, from several hundred eggs.

It is of significant importance to point out that the egg product of this invention has been shown to be safe, non-toxic, ideal for long term use and has no side effects other than on humans allergic to eggs. The egg product can be orally administered either alone or in combination with drug therapy, for long term use for diarrhea-related disorders.

The advantageous properties of this invention can be observed by reference to the following examples that illustrate the invention.

EXAMPLES

Example 1

Preparation of PL-100 Vaccine

A bacterial culture containing the spectrum of bacteria shown in Table 1 below, as obtained from the American Type Culture Collection, was reconstituted with 15 mL of media and incubated overnight at 37 C. Once good growth was obtained, approximately one-half of the bacterial suspension was employed to inoculate one liter of broth with the inoculate being incubated at 37 C.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet was resuspended in a small amount of double distilled water.

The media-free bacterial suspension was killed by placing the suspension in a glass flask in an 80 C. water bath overnight. The viability if the broth culture was tested with a small amount of killed bacteria, incubated at 37 C. for five days and checked daily for growth to certify that the bacteria had been killed.

The killed bacteria were lyophilized until dry. The dry bacteria were then mixed with sterile saline solution to a concentration of $2.2 \times 10^8$ bacterial cells/mL saline (1.0 optical density reading at 660 nm). Bacteria contained in S-100 vaccine are listed in Table 1 below.

TABLE 1

| PL-100 Bacterial List | |
|---|---|
| Escherichia coli | Escherichia coli (Aerobacter) |
| Klebsiella pneumoniae | Pseudomonas aeruginosa |
| Salmonella typhimurium | Shigella dysenteriae |
| Salmonella enteritidis | Staphylococcus epidermis |
| Staphylococcus | Streptococcus pyogenes, type 1 |
| Streptococcus pyogenes, type 3 | Streptococcus pyogenes, type 5 |
| Streptococcus pyogenes, type 8 | Streptococcus pyogenes, type 12 |
| Streptococcus pyogenes, type 14 | Streptococcus pyogenes, type 18 |
| Streptococcus pyogenes, type 22 | Proteus vulgaris |
| Streptococcus agalactiae | Streptococcus mitis |
| Streptococcus mutans | Streptococcus salavarius |
| Streptococcus sanguis | Streptococcus pneumoniae |
| Propionibacterium acnes | Haemophilis influenzae |

Immunization Procedure for Hyperimmune Egg Product

A killed preparation of pathogens was prepared as described above. For the first vaccination, the bacteria were mixed with complete Freund's adjuvant, and 5.6 mg of bacterial material were injected into the breast muscle of a chicken. For the remaining vaccines, the bacterial preparation was mixed with incomplete Freund's adjuvant and injected into the chickens at two week intervals for six months.

Eggs were collected from the hyperimmunized chickens and then spray dried into a powder form. During the spray drying procedure, inlet temperatures did not exceed 320 Degrees F., exhaust temperatures were maintained in accordance with producing powder in the range of 3.0 to 4.0 percent finished moisture, and pump pressure was maintained around 2500 to 4000 P.S.I. Lower temperatures ranging from 100–160 F. were used, and samples were monitored for moisture content during the drying process to obtain a final product having any consistency desired.

Example 2

Use of Hyperimmune Egg Product in Treating Diarrhea

The purpose of these tests was to identify, characterize, and document the preventative actions of hyperimmune egg product in an experimental model of diarrhea in mice. In this model using mice, diarrhea is induced by oral administration of castor oil. This test is a standard test for anti-diarrheal agent for human use and was used for the discovery of the two most utilized anti-diarrheal agent, loperamide and diphenoxylate.

Method

These studies were performed at Product Safety Laboratories, East Brunswick, N.J. Male mice weighing 25–30 grams were obtained from Ace Laboratories, Boyertown, Pa. They were quarantined for at least 5 days and then randomized into groups of 10 and placed in plastic boxes with bedding. Treatments were all administered by gavage to fed mice on two consecutive days between 8:00 and 9:00 A.M. Mice were given 4.0 grams/kg po of either powdered immune or powdered control egg in 20 mL/kg distilled water. Spray-dried hyperimmune egg powder was provided by DCV, Inc., Wilmington, Del. It was obtained from eggs of chickens that have been repeatedly vaccinated with large amounts of killed enteric pathogens of human origin. Sprayed-dried table eggs were used as the control. One hour after treatment on the second day of gavage, a dose of 0.3 mL of castor oil was administered by gavage. Mice were then placed in individual wire-bottomed cages and fecal output observed and recorded at 2, 4, and 6 hours after castor oil administration. A positive or negative response was used to assess the presence of diarrhea. The number of normal, soft or loose stools was also recorded. Stools were rated either normal or diarrheal at each of these time periods. Results are expressed as the number of mice with diarrheal stools.

Test A: Mice were dosed with:

1. Control egg—DCV Product A-98-06-Jan ID #843 lot 951600FB.
   PSL 80108 3D—4.0 grams/kg PO
2. Hyperimmune egg—DCV Product B-98-06-Jan ID #3059 lot 96298VOFP
   PSL 80108 4D—4.0 grams/kg PO Test B: Mice were dosed with:

1. Distilled water—20 mL/kg PO
2. Hyperimmune egg—DCV Product B-98-06-Jan ID #3059 lot 96298VOFP
   PSL 80108 4D—1.0 grams/kg PO
3. Hyperimmune egg—DCV Product B-98-06-Jan ID #3059 lot 96298 VOFP
   PSL 80108 4D—2.0 grams/kg PO
4. Hyperimmune egg—DCV Product B-98-06-Jan ID #3059 lot 96298 VOFP
   PSL 80108 4D—4.0 grams/kg PO Data Analysis and Statistics Results were analyzed using an all or none criterion, with ano-genital staining and soft stools counting as diarrhea. Results are given as percentage of mice with diarrhea at each time and the cumulative number of positives over the 6 hour period. Percent inhibition was calculated by comparison to the appropriate control. Statistical analysis was done using the chi square test.

Results

Results of the study are shown in Table 2. Data is presented as percent of mice with diarrhea and as percent inhibition compared to control for studies 1 and 2. The initial study (Test A) comparing hyperimmune egg to control egg showed a significant difference in the ability to inhibit castor oil induced diarrhea by the hyperimmune egg. Four grams/kg of hyperimmune egg significantly blocked castor oil induced diarrhea in the test subjects at the 4 hour observation period when compared to normal egg. No diarrhea was noted at the 2 hour period and the smallest amount of diarrhea was found in all groups at the 6 hour period. A significant inhibition in the cumulative occurrence of diarrhea over the entire 6 hours was noted in hyperimmune egg-treated groups.

Three doses of hyperimmune egg were compared to distilled water in the second study (Test B). All groups were dosed on two consecutive days. On the second day, castor oil was administered and the study was performed in a similar manner to Test A. There was a minimal occurrence of diarrhea noted in the first observation period. However, significant diarrhea was noted in the control treated mice at the 4 and 6 hour observation period. Hyperimmune egg administered at 1 gram/kg did not show significant anti-diarrheal activity at any time period. Hyperimmune egg, administered at 2 grams/kg showed significant activity at the 6 hour period but not at 2 or the cumulative 0–6 hour period. Hyperimmune egg administered at 4 grams per kg had significant effects at all time periods in which diarrhea was noted in the control period. Percent inhibition for castor oil diarrhea over the 0–6 hour period was dose related with 38% inhibition with 1 gram/kg, 43% with 2 grams/kg and 62% with 4 grams/kg. An estimated 50% effective dose would be between 2 and 4 grams/kg.

Discussion

Hyperimmune egg product demonstrated significant dose related activity against castor oil induced diarrhea. Four grams/kg orally as a bolus dose was effective in both studies and appears to be a reasonable therapeutic dose. The mode of action of the hyperimmune egg against castor oil is believed to be due to certain immune modulating factors in the hyperimmune egg product that act as anti-diarrheal agents. Hyperimmune egg was not effective in previous studies in which it was administered in the diet. This may have been due to a lack of an effective concentration of hyperimmune egg at sites of activity.

Hyperimmune egg may find use as acute therapy as an antidiarrheal in both animals and humans. This study shows that long periods of pretreatment are not needed for showing activity and that it is effective when given orally in a bolus dose.

TABLE 2

Castor Oil Induced Diarrhea-Chronic dosing with Nutriceuticals

| Treatment | Dose g/kg PO | 2 hr | % | 4 hr | % | 6 hr | % | 0–6 hr | % | % inh |
|---|---|---|---|---|---|---|---|---|---|---|
| Test A |  |  |  |  |  |  |  |  |  |  |
| Control Egg E80108-3D | 4 | 0/10 | 0 | 9/10 | 90 | 3/10 | 30 | 12/30 | 40 | — |
| Egg protein E80108-4D | 4 | 0/10 | 0 | 2/10* | 20 | 2/10 | 20 | 4/30* | 13 | 68 |
| Test B |  |  |  |  |  |  |  |  |  |  |
| Vehicle | 0 | 1/10 | 10 | 10/10 | 100 | 10/10 | 100 | 21/30 | 70 | — |
| Egg Protein E8010808-4D | 1 | 1/10 | 10 | 6/10 | 60 | 6/10 | 60 | 13/30 | 43 | 38 |
|  | 2 | 1/10 | 10 | 7/10 | 70 | 4/10* | 40 | 12/30 | 40 | 43 |
|  | 4 | 0/10 | 0 | 4/10* | 40 | 2/10* | 20 | 8/30* | 27 | 62 |

Example 3

Materials and Methods

Subjects

HIV positive male subjects (as documented by ELISA and Western Blot analysis) ranging in age from 18–50 years and suffering from gastrointestinal problems were recruited from the Jamshedji Jeejiboy (J.J.) Hospital, Mumbai, India. These individuals had been previously diagnosed with one or more of the AIDS defining secondary conditions (refs). None had participated in any investigational drug tests within the last 60 days or had been exposed to any innumomodulator or vaccine for the past 90 days. Subjects who had frequent changes in dosing or types of medication to control clinical symptoms, alcohol or substance abusers, history of allergy towards eggs or any other ingredient in the test article were excluded from the study.

Study Design

The open-label study testing of a dietary supplement fortified with hyperimmune egg in spray dried form (DCV, Inc. Wilmington Del. U.S.A.) was conducted for a total of 12 weeks. The dietary supplement beverage was freshly prepared and consumed as a liquid once a day for 8 weeks. At the end of this 2 month period, test article was no longer consumed for the rest of the 1 month duration of the study. The same physician monitored subjects at four week intervals for the entire length of the study and drew blood samples. All subjects maintained their normal diets and medication and were monitored during the 60-day trial period and 30 days thereafter, for any untoward signs or symptoms. The severity, onset date, duration, frequency, study product relationship, action taken and outcome of each adverse experiences were recorded.

All subjects were required to visit the physician prior to starting the study (baseline visit) and thereafter at four week intervals for a total of four visits. During each visit, the subject received a detailed physical examination and general evaluation of their well being with a list of questions that included a) estimation of frequency of bowel movements and b) consistency of bowel movements, among others.

Two case reports are presented from the study:

Case 1

Subject #1 was admitted with a weight of 46 kg. He had complaints of gripping abdominal pain, nausea, vomiting, diarrhea and was being treated with antispasmodics/antidiarrheal medicines and administration of I.V. fluids.

During the 8 wk trial period, the subject reported reduction in his bouts of nausea and diarrhea. The general well being of the subject appeared improved and he experienced a weight gain from 46 kg to 47.5 kg. (Table 1)

Case 2

Subject #2 was admitted with a weight of 53 kg. He complained of respiratory distress and abdominal pain and was treated for Koch's infection. Subject had tested HIV positive for last 6 years and had taken sporadic doses of ayurvedic medicines for chest congestion and cough. Subject was also provided antibiotics and cough syrup.

After eight weeks of consuming the test article, he showed improvement in health and general well being along with a weight gain of 3 kg. His attacks of abdominal pain and respiratory distress were reduced drastically after four weeks on the product.

Responses of Subjects

Of the 17 subjects enrolled in the study, 15 (88.2%) showed weight increases, ranging in gains from 0.5 kg to 6 kg. In some cases, weight gains amounted to a 10% increase over their initial weights. Quality of life indexes as assessed by the physician showed a marked improvement both in the physical and emotional status of the subjects. Most relevantly, many subjects also experienced a major reduction, or complete abolition, of the number of diarrheal episodes.

What is claimed is:

1. A method for treating and preventing diarrheal symptoms in a subject animal, the method comprising hyperimmunizing an egg-producing animal, collecting egg or egg product from an egg of the hyperimmunized egg-producing animal, and administering an effective amount of the egg or egg product to the subject animal, wherein hyperimmunizing the egg-producing animal comprises treating the egg-producing animal with a vaccine comprising at least one immunogen from an organism, and wherein the subject animal is free of infection from the organism.

2. The method of claim 1 wherein at least one immunogen is selected from the group consisting of bacterial, viral protozoan, fungal and cellular immunogenic and mixtures thereof.

3. The method of claim 2, wherein in the vaccine consists of a mixture of bacterial immunogens, said mixture comprising at least one immunogen from each of the following bacterial strains:

Escherichia coli, Escherichia coli (Aerobacter); Klebsiella pneumonia; Pseudomonas aeruginosa; Salmonella typhimurium; Shigella dysenteriae; Salmonella enteritidis; Staphylococcus epidermis; Staphylococcus simulans; Streptococcus pyogenes, type1; Streptococ-

*cus pyogenes,* type 3; *Streptococcus pyogenes,* type 5; *Streptococcus pyogenes,* type 8; *Streptococcus pyogenes,* type 12; *Streptococcus pyogenes,* type 14; *Streptococcus pyogenes,* type 18 *Streptococcus pyogenes,* type 22; *Proteus vulgaris; Streptococcus agalactiae; Streptococcus mitis; Streptococcus mutans; Streptococcus salavarius; Streptococcus sanguis; Streptococcus pneumoniae; Propionibacterium acnes;* and *Haemophilis influenzae.*

4. The method of claim 1 wherein the effective amount of the egg or egg product administered to the subject animal ranges from 0.5–6 grams or egg or egg product per kilogram of subject animal weight per day.

5. The method of claim 4 wherein the effective amount of the egg or egg product administered to the subject animal is 4 grams of egg or egg product per kilogram of subject animal weight.

6. The method of claim 1 wherein the egg product is administered parenterally, subcutaneously, intravenously, intramuscularly, intraperitoneally, intranasally, orally or topically.

7. A method for treating diarrheal symptoms in a subject animal, the method comprising hyperimmunizing an egg-producing animal, collecting egg or egg product from an egg of the hyperimmunized egg-producing animal, and administering an effective amount of the egg or egg product to the subject animal, wherein hyperimmunizing the egg-producing animal comprises treating the egg-producing animal with a vaccine comprising at least one immunogen-coding DNA construct, and wherein the subject animal is free of infection from the immunogen-coding DNA construct.

8. The method of claim 7 wherein at least one immunogen-coding DNA construct is selected from the group consisting of fragments of naked DNA, plasmid DNA, viral DNA, bacterial DNA, DNA expression libraries, DNA-RNA immunogens, DNA-protein conjugates and DNA liposome conjugates, and mixtures thereof.

9. The method of claim 7 wherein the egg or egg product is administered parenterally, subcutaneously, intravenously, intramuscularly, intraperitoneally, intranasally, orally or topically.

10. The method of claim 7 wherein the effective amount of the egg or egg product administered to the subject animal ranges from 0.5–6 grams of egg or egg product per kilogram of subject animal weight per day.

11. The method of claim 10 wherein the effective amount of the egg or egg product administered to the subject animal is 4 grams of egg or egg product per kilogram of subject animal weight.

* * * * *